(12) United States Patent
Ishihara et al.

(10) Patent No.: US 8,501,667 B2
(45) Date of Patent: Aug. 6, 2013

(54) WATER-BASED HERBICIDAL SUSPENSION

(75) Inventors: Yoshiaki Ishihara, Kasatsu (JP);
Tatsuhiko Tsuruta, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 1288 days.

(21) Appl. No.: 11/997,374

(22) PCT Filed: Jul. 24, 2006

(86) PCT No.: PCT/JP2006/315065
§ 371 (c)(1),
(2), (4) Date: Jan. 30, 2008

(87) PCT Pub. No.: WO2007/018060
PCT Pub. Date: Feb. 15, 2007

(65) Prior Publication Data
US 2010/0093539 A1 Apr. 15, 2010

(30) Foreign Application Priority Data

Aug. 10, 2005 (JP) .................................. 2005-231841
Nov. 10, 2005 (JP) .................................. 2005-326623

(51) Int. Cl.
*A01N 59/14* (2006.01)
*A01N 59/00* (2006.01)

(52) U.S. Cl.
USPC ........... 504/122; 504/123; 504/124; 504/125; 504/187

(58) Field of Classification Search
None
See application file for complete search history.

(56) References Cited

U.S. PATENT DOCUMENTS

H1711 H * 2/1998 Smith, III ...................... 504/136

FOREIGN PATENT DOCUMENTS

| EP | 0 124 295 | 11/1984 |
| EP | 0 365 484 | 4/1990 |
| EP | 0 514 768 | 11/1992 |
| EP | 1 277 405 | 1/2003 |
| JP | 59-205305 | 11/1984 |
| JP | 08-034702 | 2/1996 |
| JP | 2000-072602 | 3/2000 |
| JP | 2000 159603 | 6/2000 |
| JP | 3175850 | 6/2001 |
| JP | 2004-043322 | 2/2004 |
| WO | 2005 082148 | 9/2005 |

OTHER PUBLICATIONS

JP 2000-72602 A machine translation, 2000.*
Moldovan Office Action issued Oct. 15, 2010, in Patent Application No. a 2008 0006.
"Nicosulfuron" http://rupest.ru/ppdb/nicosulfuron.html, 1990, pp. 1-14.
"Flazasulfuron", http://belgiss.org.by/russian/inform/doc/pescicidu.doc, Mar. 10, 2004, pp. 1-17.
"Bensulfuron-methyl", http://rupest.ru/ppdb/bensulfuron-methyl.html, 1985, pp. 1-13.
"Azimsulfuron", http://rupest.ru/ppdb/azimsulfuron.html, 1995, pp. 1-13.
Office Action mailed Jun. 5, 2012, Issued in the corresponding Japanese application No. 2006-197578 with English Translation.

* cited by examiner

*Primary Examiner* — Alton Pryor
(74) *Attorney, Agent, or Firm* — Oblon, Spivak, McClelland, Maier & Neustadt, L.L.P.

(57) ABSTRACT

Not so many reports on the practical use of herbicidal sulfonylurea compounds have been made since they easily decompose in water or a process for production of their suspensions is complicated. Therefore, it is desired to prepare a water-based herbicidal suspension in which a herbicidal sulfonylurea compound will not decompose in water and excellent suspensibility of which is maintained, without complicated process. A water-based herbicidal suspension comprising (1) a herbicidal sulfonylurea compound (excluding 1-[3-[(4,6-dimethoxypyrimidin-2-ylcarbamoyl)sulfamoyl]-2-pyridyl]-2-fluoropropyl methoxyacetate and N-[(4,6-dimethoxypyrimidin-2-yl)aminocarbonyl]-2-(2-fluoro-1-hydroxypropyl)-3-pyridinesulfonamide) or its salt, (2) an inorganic salt, (3) at least one sulfonate selected from the group consisting of an aryl sulfonate, an alkylaryl sulfonate and their formaldehyde condensates and (4) water.

11 Claims, No Drawings

WATER-BASED HERBICIDAL SUSPENSION

TECHNICAL FIELD

The present invention relates to a water-based herbicidal suspension in which decomposition of a herbicidal sulfonylurea compound or its salt in water is suppressed and excellent suspensibility of which is maintained.

BACKGROUND ART

Heretofore, various herbicides have been developed and put into practical use for the purpose of protecting crop plants in agricultural fields and controlling weeds in non-agricultural fields. In general, the application form of such herbicides may be a solid preparation to be directly spread such as dust or granules, a solid preparation to be diluted with water and spread at the time of its use such as a wettable powder or water dispersible granules, or a liquid suspension comprising an active ingredient together with a surfactant, etc. suspended in water, a vegetable oil or the like, to be diluted with water and spread at the time of its use.

When the solid preparation to be directly spread or the solid preparation to be diluted with water at the time of its use is handled, the user may aspirate the solid flying in the air at the time of its use in some cases, and to avoid this, the liquid suspension is preferred. Further, in order to easily measure and adjust the amount of the preparation from such a reason that the area of the site to which the preparation is to be applied is different from the area per package of the preparation, a liquid preparation which can easily be measured by e.g. a scale on a preparation bottle is advantageous to a solid preparation which requires a meter such as a balance to measure its weight. Further, among liquid suspensions, a suspension in a vegetable oil is used for agricultural fields for grain in many cases, and when such a suspension in a vegetable oil is applied to non-agricultural fields such as roads, railway tracks, factory sites and play grounds, orchards and mulberry fields, the vegetable oil component will temporarily remain on the ground after the application, such being inconvenient when the field is used after the application. Further, it is preferred not to use an organic solvent, etc. to be used for an emulsifiable concentrate, etc. as far as possible in view of the influence over the environment at the application site and flammability of the preparation. Therefore, it has been desired to prepare a water-based herbicidal suspension having an active ingredient stably suspended in water.

As a compound to be incorporated as an active ingredient for herbicides, a sulfonylurea compound or its salt has been used as an active ingredient for various herbicides since it is a compound having excellent herbicidal effects with a relatively small amount of application. However, the sulfonylurea compound or its salt to be incorporated as a herbicidally active ingredient tends to easily decompose during preservation. If the active ingredient concentration in the preparation decreases by the decomposition, no expected herbicidal effect will be achieved at the time of application, or the internal pressure in a storage container for the suspension may increase during the preservation by generation of a gas due to the decomposition, which leads to blowing of the suspension at the time of opening and cause various inconvenience such as stains on the user or the circumference with the content.

Heretofore, addition of various compounds has been studied so as to prevent decomposition of the sulfonylurea compound or its salt to be incorporated as a herbicidally active ingredient. For example, JP-A-2000-159603 discloses a water-based herbicidal suspension comprising a herbicidal sulfonylurea compound and a phenol sulfonate or its formaldehyde condensate.

Further, JP-A-59-205305 discloses a water-based herbicidal suspension comprising a salt'of a herbicidal sulfonylurea compound and an ammonium or alkali metal salt of a carboxylic acid or an inorganic acid. Specifically, it is disclosed that at the time of preparation of the water-based herbicidal suspension, a herbicidal sulfonylurea compound and a surfactant are mixed in water, and an ammonium salt or an alkali metal salt of a carboxylic acid or an inorganic acid is charged thereto, whereby a salt of the herbicidal sulfonylurea compound is formed and precipitated, and the precipitated salt of the herbicidal sulfonylurea compound is dispersed in water by e.g. a wet-mill.

Further, Japanese Patent No. 3,175,850 discloses preparation of a water-based suspension of pyrazosulfuron by employing an inorganic acid, an organic acid or a buffer solution.

DISCLOSURE OF THE INVENTION

Object to be Accomplished by the Invention

Even when the above-described prior art is applied, the herbicidal sulfonylurea compound as an active ingredient to be used in the present invention easily decomposes in water, or a process for production of its suspension is complicated, and thus not so many reports on its practical use have been made. Accordingly, preparation of a water-based herbicidal suspension in which the herbicidal sulfonylurea compound will not decompose in water and excellent suspensibility of which is maintained, without complicated process, has been required.

Means to Accomplish the Object

The present inventors have conducted extensive studies to accomplish the above object. As a result, they have found that a water-based herbicidal suspension in which the herbicidal sulfonylurea compound will not decompose in water and excellent suspensibility of which is maintained can be prepared without complicated process by use of an inorganic salt and a sulfonate as a specific surfactant, and accomplished the invention.

Namely, the present invention relates to a water-based herbicidal suspension comprising (1) a herbicidal sulfonylurea compound (excluding 1-[3-[(4,6-dimethoxypyrimidin-2-ylcarbamoyl)sulfamoyl]-2-pyridyl]-2-fluoropropyl methoxyacetate and N-[(4,6-dimethoxypyrimidin-2-yl)aminocarbonyl]-2-(2-fluoro-1-hydroxypropyl)-3-pyridinesulfonamide) or its salt, (2) an inorganic salt, (3) at least one sulfonate selected from the group consisting of an aryl sulfonate, an alkylaryl sulfonate and their formaldehyde condensates and (4) water, and a method for controlling undesired plants or inhibiting their growth by using it.

The present invention further relates to a method for stabilizing a herbicidal sulfonylurea compound (excluding 1-[3-[(4,6-dimethoxypyrimidin-2-ylcarbamoyl)sulfamoyl]-2-pyridyl]-2-fluoropropyl methoxyacetate and N-[(4,6-dimethoxypyrimidin-2-yl)aminocarbonyl]-2-(2-fluoro-1-hydroxypropyl)-3-pyridinesulfonamide) or its salt in a water-based herbicidal suspension by using an inorganic salt and at least one sulfonate selected from the group consisting of an aryl sulfonate, an alkylaryl sulfonate and their formaldehyde condensates.

The present invention still further relates to a method for producing a water-based herbicidal suspension which comprises mixing at least (1) a herbicidal sulfonylurea compound (excluding 1-[3-[(4,6-dimethoxypyrimidin-2-ylcarbamoyl)sulfamoyl]-2-pyridyl]-2-fluoropropyl methoxyacetate and N-[(4,6-dimethoxypyrimidin-2-yl)aminocarbonyl]-2-(2-fluoro-1-hydroxypropyl)-3-pyridinesulfonamide) or its salt, (2) an inorganic salt, (3) at least one sulfonate selected from the group consisting of an aryl sulfonate, an alkylaryl sulfonate and their formaldehyde condensates and (4) water, followed by wet-milling if desired.

Effects of the Invention

The present invention provides a water-based herbicidal suspension in which decomposition of a herbicidal sulfonylurea compound or its salt is suppressed, and the suspensibility of which is sufficiently maintained, and a method for controlling undesired plants using it. Further, according to the present invention, the water-based herbicidal suspension can be prepared by mixing the respective components for the suspension and wet-milling the mixture if desired, without complicated production steps such as dissolution of the active ingredient and reprecipitation.

BEST MODE FOR CARRYING OUT THE INVENTION

The herbicidal sulfonylurea compound to be used in the present invention is at least one member selected from the group of compounds having the following partial structure as the chemical structure:

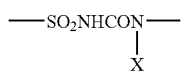

(wherein X is a hydrogen atom or an alkyl group) (excluding 1-[3-[(4,6-dimethoxypyrimidin-2-ylcarbamoyl)sulfamoyl]-2-pyridyl]-2-fluoropropyl methoxyacetate and N-[(4,6-dimethoxypyrimidin-2-yl)aminocarbonyl]-2-(2-fluoro-1-hydroxypropyl)-3-pyridinesulfonamide), and it may, for example, be chlorimuron-ethyl, sulfometuron-methyl, primisulfuron-methyl, bensulfuron-methyl, chlorsulfuron, metsulfuron-methyl, cinosulfuron, pyrazosulfuron-ethyl, azimsulfuron, flazasulfuron, rimsulfuron, nicosulfuron, imazosulfuron, cyclosulfamuron, prosulfuron, flupyrsulfuron, triflusulfuron-methyl, halosulfuron-methyl, thifensulfuron-methyl, ethoxysulfuron, oxasulfuron, ethametsulfuron, iodosulfuron, sulfosulfuron, triasulfuron, tribenuron-methyl, tritosulfuron, foramsulfuron, trifloxysulfuron, isosulfuron-methyl, mesosulfuron-methyl, orthosulfamuron or amidosulfuron. Among them, preferred is nicosulfuron, flazasulfuron, bensulfuron-methyl or azimsulfuron.

As the salt of the above sulfonylurea compound, various salts may be mentioned. It may, for example, be a salt with an alkali metal such as sodium or potassium, a salt with an alkaline earth metal such as magnesium or calcium, or a salt with an amine such as monomethylamine, dimethylamine or triethylamine.

As the inorganic salt to be used in the present invention, various inorganic salts may be mentioned. It may, for example, be an alkali metal phosphate or an alkaline earth metal phosphate. Preferred is an alkali metal phosphate, and particularly preferred is sodium dihydrogenphosphate or potassium dihydrogenphosphate.

The alkyl moiety in the sulfonate to be used in the present invention may be linear or branched. It may, for example, be a $C_{1-12}$ alkyl moiety such as methyl, ethyl, propyl, butyl, pentyl, hexyl, heptyl, octyl, nonyl, decyl, undecyl or dodecyl.

The aryl moiety in the sulfonate may be a monocyclic or polycyclic aryl such as a benzene ring or a naphthalene ring.

As the salt of the sulfonate, various salts may be mentioned. It may, for example, be a salt with an alkali metal such as sodium or potassium, or a salt with an alkaline earth metal such as magnesium or calcium.

The sulfonate is preferably an alkylaryl sulfonate or its formaldehyde condensate, more preferably an alkylbenzene sulfonate, an alkylnaphthalene sulfonate, an alkylbenzene sulfonate condensed with formaldehyde or an alkylnaphthalene sulfonate condensed with formaldehyde, and furthermore preferably an alkylbenzene sulfonate condensed with formaldehyde or an alkylnaphthalene sulfonate condensed with formaldehyde.

For the preparation of the water-based herbicidal suspension, various additives may be used as the case requires. Various additives which can be used here may be any additives so long as they are commonly used in this technical field, and for example, another surfactant (a surfactant other than the sulfonate), a solvent, an anti-settling agent, a thickener, an antifoaming agent, an antifreezing agent, a gelling agent, a dispersion stabilizer, a phytotoxicity reducing agent, an anti-mold agent, a preservative, and an inorganic ammonium salt, may be mentioned. The following may, for example, be mentioned as specific examples of such various additives. Further, such formulations may be prepared in accordance with methods commonly employed in this technical field.

The another surfactant includes, for example, anionic surfactants such as a salt of fatty acid, a benzoate, an alkylsulfosuccinate, a dialkylsulfosuccinate, a polycarboxylate, a salt of alkylsulfuric acid ester, an alkyl sulfate, an alkyl diglycol ether sulfate, a salt of alcohol sulfuric acid ester, an alkyl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a polyoxyethylene styrylaryl ether sulfate, an ammonium polyoxyethylene styrylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a polyoxyethylene styrylaryl ether phosphoric acid ester or its salt, a phenol sulfonate condensed with formaldehyde and a salt of maleic anhydride alkylene copolymer; nonionic surfactants such as a sorbitan fatty acid ester, a glycerin fatty acid ester, a fatty acid polyglyceride, a fatty acid alcohol polyglycol ether, an acetylene glycol, an acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene hydrogenated castor oil, a polyoxyethylene castor oil and a polyoxypropylene fatty acid ester, and cationic surfactants such as an alkoxylated fatty amine. If desired, two or more of them may suitably be used in combination.

The anti-settling agent may, for example, be silica, bentonite-alkylamino complex, bentonite, white carbon or aluminum magnesium silicic acid. If desired, two or more of them may be suitably used in combination.

The thickener may, for example, be a heteropolysaccharide such as xanthan gum or guar gum, a water-soluble polymer such as polyvinyl alcohol, a sodium salt of carboxymethyl cellulose or sodium alginate, bentonite or white carbon. If desired, two or more of them may suitably be used in combination.

The antifoaming agent may, for example, be polydimethylsiloxane or acetylene alcohol. If desired, two or more of them may suitably be used in combination.

The antifreezing agent may, for example, be ethylene glycol, propylene glycol, glycerin or urea. If desired, two or more of them may suitably be used in combination.

The preservative may, for example, be formalin, p-chloro m-xylenol or 1,2-benzisothiazolin-3-one. If desired, two or more of them may suitably be used in combination.

The solvent may, for example, be a monohydric alcohol such as propanol or isobutanol; a polyhydric alcohol such as ethylene glycol, propylene glycol, diethylene glycol, hexylene glycol, polyethylene glycol, polypropylene glycol or glycerol; a glycol ether such as propylcellosolve, butylcellosolve, phenylcellosolve, propylene glycol monomethyl ether, propylene glycol monoethyl ether, propylene glycol monopropyl ether, propylene glycol monobutyl ether or propylene glycol monophenyl ether; an ether such as dioxane; a ketone such as cyclohexanone or methyl isobutyl ketone; a fatty acid such as acetic acid or butyric acid; an ester such as isopropyl acetate or butyl acetate; a nitrogen-containing/sulfur-containing solvent such as N-methylformamide, N-methylpyrrolidone, dimethyl sulfoxide, 1,3-dimethyl-2-imidazolidinone, an amine or an ether amine; an aliphatic hydrocarbon such as normal paraffin or isoparaffin; or an aromatic hydrocarbon such as an alkylbenzene, an alkylnaphthalene or phenylxylylethane. If desired, two or more of them may suitably be used in combination.

In the present invention, if desired, another herbicidal compound other than the above mentioned herbicidal sulfonylurea compound or its salt may be used in combination, whereby more excellent effects and functionality may be achieved in some cases. For example, the range of plants to be killed may be broadened, the stage at which the herbicidal suspension is applied may be broadened, or the herbicidal activity may be improved in some cases. The herbicidal sulfonylurea compound or its salt and the another herbicidal compound may be separately prepared and mixed at the time of application, or they may be prepared into one water-based herbicidal suspension. The present invention includes the above combined water-based herbicidal suspension and a method of controlling undesired plants or inhibiting their growth by means of such a suspension. Further, the present invention includes a method for controlling undesired plants or inhibiting their growth, by using separate preparations of the herbicidal sulfonylurea compound or its salt and the another herbicidal compound.

As the another herbicidal compound which can be used in combination with the herbicidal sulfonylurea compound or its salt, the compound groups of the following (1) to (11) (common names; a part thereof is under application for ISO) may, for example, be mentioned. Even when not specifically mentioned, in a case where such compounds have salts, alkyl esters or various structural isomers such as optical isomers, they are, of course, all included.

(1) Those which are believed to exhibit herbicidal effects by disturbing hormone activities of plants, such as a phenoxy type such as 2,4-D, 2,4-DB, 2,4-DP, MCPA, MCPB, MCPP or naproanilide, an aromatic carboxylic acid type such as 2,3,6-TBA, dicamba, dichlobenil, picloram, triclopyr, clopyralid or aminopyralid, and others such as naptalam, benazolin, quinclorac, quinmerac, diflufenzopyr and thiazopyr.

(2) Those which are believed to exhibit herbicidal effects by inhibiting photosynthesis of plants, such as a urea type such as chlorotoluron, diuron, fluometuron, linuron, isoproturon, metobenzuron or tebuthiuron, a triazine type such as simazine, atrazine, atratone, simetryn, prometryn, dimethametryn, hexazinone, metribuzin, terbuthylazine, cyanazine, ametryn, cybutryne, triaziflam or propazine, a uracil type such as bromacil, lenacil or terbacil, an anilide type such as propanil or cypromid, a carbamate type such as swep, desmedipham or phenmedipham, a hydroxybenzonitrile type such as bromoxynil, bromoxynil-octanoate or ioxynil, and others such as pyridate, bentazone, amicarbazone and methazole.

(3) Quaternary ammonium salt type such as paraquat or diquat, which is believed to be converted to free radicals by itself to form active oxygen in the plant body.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen-sodium, fomesafen, oxyfluorfen, lactofen or ethoxyfen-ethyl, a cyclic imide type such as chlorphthalim, flumioxazin, flumiclorac-pentyl or fluthiacet-methyl, and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, metobenzuron, cinidon-ethyl, flupoxam, fluazolate, profluazol, pyrachlonil, flufenpyr-ethyl and bencarbazone.

(5) Those which are believed to exhibit herbicidal effects characterized by whitening activities by inhibiting chromogenesis of plants such as carotenoids, such as a pyridazinone type such as norflurazon, chloridazon or metflurazon, a pyrazole type such as pyrazolate, pyrazoxyfen, benzofenap, topramezone (BAS-670H) or pyrasulfotole, and others such as amitrol, fluridone, flurtamone, diflufenican, methoxyphenone, clomazone, sulcotrione, mesotrione, AVH-301, isoxaflutole, difenzoquat, isoxachlortole, benzobicyclon, picolinafen and beflubutamid.

(6) Those which exhibit strong herbicidal effects specifically to gramineous plants, such as an aryloxyphenoxypropionic acid type such as diclofop-methyl, flamprop-M-methyl, pyriphenop-sodium, fluazifop-butyl, haloxyfop-methyl, quizalofop-ethyl, cyhalofop-butyl, fenoxaprop-ethyl or metamifop-propyl, and a cyclohexanedione type such as alloxydim-sodium, clethodim, sethoxydim, tralkoxydim, butroxydim, tepraloxydim, caloxydim, clefoxydim or profoxydim.

(7) Those which are believed to exhibit herbicidal effects by inhibiting an amino acid biosynthesis of plants, such as a sulfonylurea type such as chlorimuron-ethyl, sulfometuron-methyl, primisulfuron-methyl, bensulfuron-methyl, chlorsulfuron, metsulfuron-methyl, cinosulfuron, pyrazosulfuron-ethyl, azimsulfuron, flazasulfuron, rimsulfuron, nicosulfuron, imazosulfuron, cyclosulfamuron, prosulfuron, flupyrsulfuron, triflusulfuron-methyl, halosulfuron-methyl, thifensulfuron-methyl, ethoxysulfuron, oxasulfuron, ethametsulfuron, iodosulfuron, sulfosulfuron, triasulfuron, tribenuron-methyl, tritosulfuron, foramsulfuron, trifloxysulfuron, isosulfuron-methyl, mesosulfuron-methyl, orthosulfamuraon or amidosulfuron, a triazolopyrimidinesulfonamide type such as flumetsulam, metosulam, diclosulam, cloransulam-methyl, florasulam, metosulfam or penoxsulam, an imidazolinone type such as imazapyr, imazethapyr, imazaquin, imazamox, imazameth, imazamethabenz or imazapic, a pyrimidinylsalicylic acid type such as pyrithiobac-sodium, bispyribac-sodium, pyriminobac-methyl, pyribenzoxim, pyriftalid or pyrimisulfan (KUH-021), a sulfonylaminocarbonyltriazolinone type such as flucarbazone or procarbazone-sodium, and others such as glyphosate, glyphosate-ammonium, glyphosate-isopropylamine, sulfosate, glufosinate, glufosinate-ammonium and bilanafos.

(8) Those which are believed to exhibit herbicidal effects by inhibiting cell mitoses of plants, such as a dinitroaniline type such as trifluralin, oryzalin, nitralin, pendimethalin, ethalfluralin, benfluralin or prodiamine, an amide type such as bensulide, napronamide or pronamide, an organic phosphorus type such as amiprofos-methyl, butamifos, anilofos or piperophos, a phenylcarbamata type such as propham, chlorpropham or barban, a cumylamine type such as daimuron, cumyluron or bromobutide, and others such as asulam, dithiopyr, thiazopyr, cafenstrole and indanofan.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor or propisochlor, a carbamate type such as molinate, dimepiperate or pyributicarb, and others such as etobenzanid, mefenacet, flufenacet, tridiphane, fentrazamide, oxaziclomefone, dimethenamid and benfuresate.

(10) A thiocarbamate type such as EPTC, butylate, vernolate, pebulate, cycloate, prosulfocarb, esprocarb, thiobencarb, diallate or triallate, and others such as MSMA, DSMA, endothall, ethofumesate, sodium chlorate, pelargonic acid, fosamine, pinoxaden and HOK-201.

(11) Those which are believed to exhibit herbicidal effects by being parasitic on plants, such as *Xanthomonas campestris, Epicoccosurus nematosurus, Exserohilum monoseras* and *Drechsrela monoceras*.

Blend proportions of the respective components in s the water-based herbicidal suspension of the present invention cannot generally be defined, since they may suitably be changed depending upon the types of the blend components, the formulations or the application situation. The proportion of the herbicidal sulfonylurea compound or its salt is from 0.1 to 60 parts by weight, preferably from 0.5 to 50 parts by weight, the proportion of the inorganic salt is from 0.1 to 25 parts by weight, preferably from 1 to 20 parts by weight, more preferably from 2 to 10 parts by weight, the proportion of the sulfonate is from 0.01 to 30 parts by weight, preferably from 0.1 to 20 parts by weight, and the main component of the rest is water.

In a case where another surfactant is incorporated if desired, its proportion is from 0.01 to 20 parts by weight, preferably from 0.1 to 15 parts by weight. In a case where an anti-settling agent is incorporated, its proportion is from 0.01 to 10 parts by weight, preferably from 0.05 to 5 parts by weight. In a case where a thickener is incorporated, its proportion is from 0.01 to 10 parts by weight, preferably from 0.05 to 5 parts by weight. In a case where an antifoaming agent is incorporated, its proportion is from 0.001 to 10 parts by weight, preferably from 0.01 to 5 parts by weight. In a case where a preservative is incorporated, its proportion is from 0.01 to 10 parts by weight, preferably from 0.05 to 5 parts by weight. In a case where a solvent is incorporated, its proportion is from 1 to 70 parts by weight, preferably from 1 to 50 parts by weight. In a case where another herbicidal compound is incorporated, its proportion is from 0.1 to 60 parts by weight, preferably from 0.1 to 50 parts by weight.

The water-based herbicidal suspension of the present invention is capable of controlling a wide range of undesired plants such as annual weeds and perennial weeds, or inhibiting their growth, by applying it to such undesired plants or to a place where they grow, for example, by foliar application, soil application or water application. The undesired plants include grasses (or gramineae) such as barnyardgrass (*Echinochloa crus-galli* L.), early watergrass (*Echinochloa oryzicola* vasing), crabgrass (*Digitaria sanguinalis* L.), greenfoxtail (*Setaria viridis* L.), giant foxtail (*Setaria faberi* Herrm.), goosegrass (*Eleusine indica* L.), wild oat (*Avena fatua* L.), johnsongrass (*Sorghum halepense* L.), quackgrass (*Agropyron repens* L.), alexandergrass (*Brachiaria plantaginea*), paragrass (*Panicum purpurascens*), sprangletop (*Leptochloa chinensis*), red sprangletop (*Leptochloa panicea*), annual bluegrass (*Poa annua* L.), black grass (*Alopecurus myosuroides* Huds.) and cholorado bluestem (*Agropyron tsukushiense* (Honda) Ohwi), sedges (or Cyperaceae) such as rice flatsedge (*Cyperus iria* L.), purple nutsedge (*Cyperus rotundus* L.), yellow nutsedge (*Cyperus esculentus* L.), japanese bulrush (*Scirpus juncoides*), flatsedge (*Cyperus serotinus*), smallflower umbrellaplant (*Cyperus difformis*), slender spikerush (*Eleocharis acicularis*) and water chestnut (*Eleocharis kuroguwai*), alismataceae such as japanese ribbon waparo (*Sagittaria pygmaea*), arrow-head (*Sagittaria trifolia*) and narrowleaf waterplantain (*Alisma canaliculatum*), pontederiaceae such as monochoria (*Monochoria Vaginalis*) and monochoria species (*Monochoria korsakowii*), scrophulariaceae such as false pimpernel (*Lindernia pyxidaria*) and abunome (*Dopatrium junceum*), lythraceae such as toothcup (*Rotala india*) and red stem (*Ammannia multiflora*), and velvetleaf (*Abutilon theophrasti* MEDIC.), tall morningglory (*Ipomoea purpurea* L.), common lambsquarters (*Chenopodium album* L.), prickly sida (*Sida spinosa* L.), common purslane (*Portulaca oleracea* L.), slender amaranth (*Amaranthus viridis* L.), redroot pigweed (*Amaranthus retroflexus* L.), sicklepod (*Cassia obtusifolia* L.), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.), common ragweed (*Ambrosia elatior* L.), catchweed (*Galium spurium* L.), field bindweed (*Calystegia arvensis* L.), jimsonweed (*Datura stramonium*), thistle (*Breea setosa* (BIEB.)KITAM.) and threeseeded copperleaf (*Acalypha australis* L.). The application range extends to agricultural fields such as crop plant fields, paddy fields, orchards and mulberry fields and non-agricultural fields such as forest land, farm roads, play grounds, factory sites and grass plots. The herbicidal sulfonylurea compound or its salt may be applied in an amount of 1 to 500 g/ha, preferably from 2 to 250 g/ha.

Now, the present invention will be described in further detail with reference to Examples. However, it should be understood that the present invention is by no means restricted to such specific Examples.

EXAMPLE 1

(1) Nicosulfuron (purity: 93.4%): 10.7 parts by weight
(2) Sodium alkylnaphthalene sulfonate condensed with formaldehyde (trade name: Supragil MNS/25, manufactured by Rhodia Nicca, Ltd.): 5.0 parts by weight
(3) Silicone antifoaming agent (trade name: Rhodorsil 432, manufactured by Rhodia Nicca, Ltd.): 0.1 part by weight
(4) Sodium dihydrogenphosphate: 8.0 parts by weight
(5) Water: 76.2 parts by weight The above components were mixed, and the mixture was milled by a wet-mill for 5 minutes to prepare a water-based herbicidal suspension.

EXAMPLE 2

(1) Nicosulfuron (purity: 93.4%): 10.7 parts by weight
(2) Supragil MNS/25 (as defined above): 5.0 parts by weight
(3) Rhodorsil 432 (as defined above): 0.1 part by weight
(4) Potassium dihydrogenphosphate: 8.0 parts by weight
(5) Water: 76.2 parts by weight
The above components were mixed, and the mixture was milled by a wet-mill for 5 minutes to prepare a water-based herbicidal suspension.

EXAMPLE 3

(1) Nicosulfuron (purity: 94.5%): 11.7 parts by weight
(2) Sodium alkylnaphthalene sulfonate (trade name: NEWKALGEN BX-C, manufactured by TAKEMOTO OIL & FAT Co., Ltd.): 4.0 parts by weight
(3) Rhodorsil 432 (as defined above): 0.1 part by weight
(4) Sodium dihydrogenphosphate: 8.0 parts by weight
(5) Water: 76.2 parts by weight
The above components were mixed, and the mixture was milled by a wet-mill for 5 minutes to prepare a water-based herbicidal suspension.

EXAMPLE 4

A water-based herbicidal suspension was prepared in the same manner as in Example 3 except that sodium alkylbenzene sulfonate (trade name: Neogen Powder, manufactured by DAI-ICHI KOGYO SEIYAKU Co., Ltd.) was used instead of NEWKALGEN BX-C.

EXAMPLE 5

(1) Flazasulfuron (purity: 95.1%): 11.56 parts by weight
(2) Supragil MNS/25 (as defined above): 4.0 parts by weight
(3) Rhodorsil 432 (as defined above): 0.1 part by weight
(4) Sodium dihydrogenphosphate: 8.0 parts by weight
(5) Water: 76.34 parts by weight
The above components were mixed, and the mixture was milled by a wet-mill for 5 minutes to prepare a water-based herbicidal suspension.

EXAMPLE 6

(1) Azimsulfuron (purity: 99%): 10.0 parts by weight
(2) Supragil MNS/25 (as defined above): 4.0 parts by weight
(3) Sodium dihydrogenphosphate: 7.0 parts by weight
(4) Water: 79.0 parts by weight
The above components were mixed, and the mixture was milled by a wet-mill for 5 minutes to prepare a water-based herbicidal suspension.

EXAMPLE 7

(1) Bensulfuron-methyl (purity: 99.3%): 10.0 parts by weight
(2) Supragil MNS/25 (as defined above): 4.0 parts by weight
(3) Sodium dihydrogenphosphate: 7.0 parts by weight
(4) Water: 79.0 parts by weight
The above components were mixed, and the mixture was milled by a wet-mill for 5 minutes to prepare a water-based herbicidal suspension.

COMPARATIVE EXAMPLE 1

(1) Nicosulfuron (purity: 93.4%): 10.7 parts by weight
(2) Supragil MNS/25 (as defined above): 5.0 parts by is weight
(3) Rhodorsil 432 (as defined above): 0.1 part by weight
(4) Water: 84.2 parts by weight
The above components were mixed, and the mixture was milled by a wet-mill for 5 minutes to prepare a water-based herbicidal suspension.

COMPARATIVE EXAMPLE 2

A water-based herbicidal suspension was prepared in the same manner as in Example 3 except that sodium phenolsulfonate (trade mane: Tamol PP, manufactured by BASF Japan Ltd.) was used instead of NEWKALGEN BX-C.

COMPARATIVE EXAMPLE 3

A water-based herbicidal suspension was prepared in the same manner as in Example 3 except that sodium polycarboxylate (trade name: NEWKALGEN WG-5, manufactured by TAKEMOTO OIL & FAT Co., Ltd.) was used instead of NEWKALGEN BX-C.

COMPARATIVE EXAMPLE 4

A water-based herbicidal suspension was prepared in the same manner as in Example 3 except that ammonium polyoxyethylene tristyrylphenyl ether sulfate (trade name: Soprophor 4D384, manufactured by Rhodia Nicca, Ltd.) was used instead of NEWKALGEN BX-C.

COMPARATIVE EXAMPLE 5

(1) Nicosulfuron (purity: 94.5%): 11.7 parts by weight
(2) NEWKALGEN BX-C (as defined above): 4.0 parts by weight
(3) Rhodorsil 432 (as defined above): 0.1 part by weight
(4) Water: 84.2 parts by weight
The above components were mixed, and the mixture was milled by a wet-mill for 5 minutes to prepare a water-based herbicidal suspension.

COMPARATIVE EXAMPLE 6

A water-based herbicidal suspension was prepared in the same manner as in Comparative Example 5 except that Neogen Powder (as defined above) was used instead of NEWKALGEN BX-C.

COMPARATIVE EXAMPLE 7

A water-based herbicidal suspension was prepared in the same manner as in Comparative Example 5 except that Tamol PP (as defined above) was used instead of NEWKALGEN BX-C.

COMPARATIVE EXAMPLE 8

A water-based herbicidal suspension was prepared in the same manner as in Comparative Example 5 except that NEWKALGEN WG-5 (as defined above) was used instead of NEWKALGEN BX-C.

COMPARATIVE EXAMPLE 9

A water-based herbicidal suspension was prepared in the same manner as in Comparative Example 5 except that Soprophor 4D384 (as defined above) was used instead of NEWKALGEN BX-C.

COMPARATIVE EXAMPLE 10

(1) Flazasulfuron (purity: 95.1%): 11.56 parts by weight
(2) Tamol PP (as defined above): 4.0 parts by weight
(3) Rhodorsil 432 (as defined above): 0.1 part by weight
(4) Sodium dihydrogenphosphate: 8.0 parts by weight
(5) Water: 76.34 parts by weight The above components were mixed, and the mixture was milled by a wet-mill for 5 minutes to prepare a water-based herbicidal suspension.

COMPARATIVE EXAMPLE 11

(1) Azimsulfuron (purity: 99%): 10.0 parts by weight
(2) Supragil MNS/25 (as defined above): 4.0 parts by weight
(3) Water: 86.0 parts by weight The above components were mixed, and the mixture was milled by a wet-mill for 5 minutes to prepare a water-based herbicidal suspension.

COMPARATIVE EXAMPLE 12

(1) Bensulfuron-methyl (purity: 99.3%): 10.0 parts by weight
(2) Supragil MNS/25 (as defined above): 4.0 parts by weight
(3) Water: 86.0 parts by weight The above components were mixed, and the mixture was milled by a wet-mill for 5 minutes to prepare a water-based herbicidal suspension.

STABILITY TEST EXAMPLE 1

Each of the water-based herbicidal suspensions prepared in Examples 1 and 2 and Comparative Example 1 was stored in a thermostatic oven at 54° C. for 14 days. The content of Nicosulfuron in the water-based herbicidal suspension before and after the storage was determined by means of liquid chromatography to calculate the decomposition rate in accordance with the following formula, thereby to evaluate the change with time. The results are shown in Table 1.

Decomposition rate (%)=[(content immediately after preparation−content after storage)/content immediately after preparation]×100

TABLE 1

| | Decomposition rate (%) |
|---|---|
| Ex. 1 | 10.3 |
| Ex. 2 | 11.8 |
| Comp. Ex. 1 | 20.1 |

It is understood from the above results in Stability Test Example 1 that decomposition of Nicosulfuron is remarkably suppressed when a sulfonate as the specific surfactant in the present invention and an inorganic salt are used, as compared with when the specific surfactant is used alone.

STABILITY TEST EXAMPLE 2

The change with time of the content of Nicosulfuron was evaluated in the same manner as in the above Stability Test Example 1 by using the water-based herbicidal suspensions prepared in Examples 3 and 4 and Comparative Examples 2 to 9. The results are shown in Table 2.

TABLE 2

| | Decomposition rate (%) |
|---|---|
| Ex. 3 | 10.6 |
| Ex. 4 | 10.1 |
| Comp. Ex. 2 | 18.4 |
| Comp. Ex. 3 | 23.0 |
| Comp. Ex. 4 | 18.1 |
| Comp. Ex. 5 | 34.8 |
| Comp. Ex. 6 | 31.4 |
| Comp. Ex. 7 | 32.7 |
| Comp. Ex. 8 | 57.4 |
| Comp. Ex. 9 | 18.9 |

It is understood from the above results in Stability Test Example 2 that decomposition of Nicosulfuron is remarkably suppressed when a sulfonate as the specific surfactant in the present invention and an inorganic salt are used, as compared with when the specific surfactant is used alone or when a surfactant other than the specific surfactant is used.

STABILITY TEST EXAMPLE 3

The change with time of the content of Flazasulfuron was evaluated in the same manner as in the above Stability Test Example 1 by using the water-based herbicidal suspensions prepared in Example 5 and Comparative Example 10. The results are shown in Table 3.

TABLE 3

| | Decomposition rate (%) |
|---|---|
| Ex. 5 | 5.67 |
| Comp. Ex. 10 | 13.41 |

It is understood from the above results in Stability Test Example 3 that decomposition of Flazasulfuron is remarkably suppressed when a sulfonate as the specific surfactant in the present invention and an inorganic salt are used, as compared with when a surfactant other than the specific surfactant is used.

STABILITY TEST EXAMPLE 4

The change with time of the content of each sulfonylurea compound was evaluated in the same manner as in the above Stability Test Example 1 by using the water-based herbicidal suspensions prepared in Examples 6 and 7 and Comparative Examples 11 and 12. The results are shown in Table 4.

TABLE 4

| | Sulfonylurea compound | Decomposition rate (%) |
|---|---|---|
| Ex. 6 | Azimsulfuron | 3.8 |
| Ex. 7 | Bensulfuron-methyl | −0.5 |
| Comp. Ex. 11 | Azimsulfuron | 11.5 |
| Comp. Ex. 12 | Bensulfuron-methyl | 12.2 |

It is understood from the above results in Stability Test Example 4 that decomposition of each sulfonylurea compound is remarkably suppressed when a sulfonate as the specific surfactant in the present invention and an inorganic salt are used, as compared with when the specific surfactant is used alone.

BIOLOGICAL TEST EXAMPLE

Upland field soil is filled in a 1/1,000,000 ha pot, seeds of a plant (crabgrass (*Digitaria sanguinalis* L.) or redroot pigweed (*Amaranthus retroflexus* L.)) are sown and grown in a green house. When the plant reaches 3 leaf stage, a pre-described amount (100 g a.i./ha) of the water-based herbicidal suspension of the present invention is diluted with water corresponding to 300 L/ha, and a spreader (trade name: Surfactant WK, manufactured by Kao Corporation) is added thereto, followed by foliar application. On the 21th day after the application, the growth of the plant is observed. As a result, the water-based herbicidal suspension of the present invention exhibits excellent herbicidal activity.

The invention claimed is:

1. A stable water-based herbicidal suspension, comprising:
   (1) a herbicidal sulfonylurea compound (excluding 1-[3-[(4,6-dimethoxypyrimidin-2-ylcarbamoyl)sulfamoyl]-2-pyridyl]-2-fluoropropyl methoxyacetate and N-[(4,6-dimethoxypyrimidin-2-yl)aminocarbonyl]-2-(2-fluoro-1-hydroxypropyl)-3-pyridinesulfonamide) or its salt;
   (2) an inorganic salt;
   (3) at least one sulfonate selected from the group consisting of an aryl sulfonate, an alkylaryl sulfonate, an aryl sulfonate formaldehyde condensate, and an alkylaryl sulfonate formaldehyde condensate; and
   (4) water,
   wherein a proportion of the inorganic salt in the water-based herbicidal suspension is from 1 to 20% by weight, and
   wherein the inorganic salt is an alkali metal phosphate.

2. The water-based herbicidal suspension according to claim 1, wherein the herbicidal sulfonylurea compound is at least one member selected from the group consisting of nicosulfuron, flazasulfuron, bensulfuron-methyl and azimsulfuron.

3. The water-based herbicidal suspension according to claim 1, wherein the alkali metal phosphate is at least one member selected from the group consisting of sodium dihydrogenphosphate and potassium dihydrogenphosphate.

4. The water-based herbicidal suspension according to claim 3, wherein the alkali metal phosphate is sodium dihydrogenphosphate.

5. The water-based herbicidal suspension according to claim 1, wherein the sulfonate is at least one member selected from the group consisting of an alkylbenzene sulfonate, an alkylnaphthalene sulfonate, an alkylbenzene sulfonate condensed with formaldehyde and an alkylnaphthalene sulfonate condensed with formaldehyde.

6. The water-based herbicidal suspension according to claim 5, wherein the sulfonate is at least one member selected from the group consisting of an alkylbenzene sulfonate condensed with formaldehyde and an alkylnaphthalene sulfonate condensed with formaldehyde.

7. The water-based herbicidal suspension according to claim 1, which further comprises another herbicidal compound.

8. A method for controlling undesired plants or inhibiting their growth, which comprises applying a herbicidally effective amount of the water-based herbicidal suspension as defined in claim 1 to the undesired plants or to a place where they grow.

9. The water-based herbicidal suspension of claim 1, wherein the proportion of the inorganic salt in the water-based herbicidal suspension is from 2 to 10% by weight.

10. A method for stabilizing a herbicidal sulfonylurea compound (excluding 1-[3-[(4,6-dimethoxypyrimidin-2-ylcarbamoyl)sulfamoyl]-2-pyridyl]-2-fluoropropyl methoxyacetate and N-[(4,6-dimethoxypyrimidin-2-yl)aminocarbonyl]-2-(2-fluoro-1-hydroxypropyl)-3-pyridinesulfonamide) or its salt in a water-based herbicidal suspension, comprising:
   stabilizing the compound with an inorganic salt and at least one sulfonate selected from the group consisting of an aryl sulfonate, an alkylaryl sulfonate, an aryl sulfonate formaldehyde condensate, and an aklylaryl sulfonate formaldehyde condensate,
   wherein a content of the inorganic salt in the water-based herbicidal suspension is from 1 to 20% by weight, and
   wherein the inorganic salt is an alkali metal phosphate.

11. The method of claim 10, wherein the content of the inorganic salt in the water-based herbicidal suspension is from 2 to 10% by weight.

* * * * *